United States Patent
Mimura et al.

(10) Patent No.: US 8,478,017 B2
(45) Date of Patent: Jul. 2, 2013

(54) METHOD FOR DISTINGUISHING LIVING CELLS DURING CELL OBSERVATION, IMAGE PROCESSING PROGRAM FOR CELL OBSERVATION, AND IMAGE PROCESSING DEVICE

(75) Inventors: Masafumi Mimura, Ageo (JP); Kei Ito, Okegawa (JP)

(73) Assignee: Nikon Corporation, Tokyo (JP)

( * ) Notice: Subject to any disclaimer, the term of this patent is extended or adjusted under 35 U.S.C. 154(b) by 262 days.

(21) Appl. No.: 12/923,144

(22) Filed: Sep. 3, 2010

(65) Prior Publication Data

US 2011/0002525 A1    Jan. 6, 2011

Related U.S. Application Data

(63) Continuation of application No. PCT/JP2009/053956, filed on Mar. 3, 2009.

(30) Foreign Application Priority Data

Mar. 4, 2008 (JP) .................................. 2008-053557

(51) Int. Cl.
*G06K 9/00* (2006.01)
(52) U.S. Cl.
USPC ........................................... 382/133; 382/216
(58) Field of Classification Search
USPC .................. 382/133, 134, 216, 218, 278, 296
See application file for complete search history.

(56) References Cited

U.S. PATENT DOCUMENTS

| 2002/0110928 A1 | 8/2002 | Yahiro ........................... 436/518 |
| 2006/0073470 A1 | 4/2006 | Noda et al. ........................ 435/4 |
| 2008/0032328 A1 | 2/2008 | Cline et al. .................... 435/40.5 |
| 2009/0086314 A1 | 4/2009 | Namba et al. ................. 359/383 |

FOREIGN PATENT DOCUMENTS

| CN | 1678751 A | 10/2005 |
| EP | 1 865 315 A1 | 12/2007 |
| JP | 2002-214228 A | 7/2002 |
| JP | 2004-229619 A | 8/2004 |
| JP | 2007-155982 A | 6/2007 |
| KR | 1020050062543 A | 6/2005 |
| WO | 03/100086 A1 | 12/2003 |
| WO | 03/102224 A1 | 12/2003 |
| WO | 2004/020656 A1 | 3/2004 |
| WO | 2007/139201 A1 | 12/2007 |

OTHER PUBLICATIONS

Yukari Sasamura et al., "A Note on an Automatic Extract Method for Apoptotic Cells from Videomicroscopy Images," ITE Technical Report (2003), vol. 27, pp. 21-24.
International Search Report for PCT/JP2009/053956, mailed Mar. 31, 2009.
Nilanjan, Ray, et al., "Tracking Leukocytes In Vivo With Shape and Size Constrained Active Contours", IEEE Transactions on Medical Imaging, vol. 21, No. 10, Oct. 2002.
European Search Report issued by the European Patent Office on Jul. 20, 2012 in the corresponding European patent application.

*Primary Examiner* — Andrew W Johns

(57) ABSTRACT

An image processing program for cell observation in which living cells can be distinguished from foreign matter other than living cells during cell observation under wide observation conditions. The image processing program includes a step for capturing first and second images of an object positioned in the observation field of view at a predetermined time interval, a step for extracting a representation of the object shown in the obtained images, steps for aligning the rotational angular orientation of the object in the image plane and computing a correlation value, a step for determining whether the object is a living cell on the basis of the computed correlation value, and steps for outputting the result of the decision made with regard to the object.

15 Claims, 8 Drawing Sheets

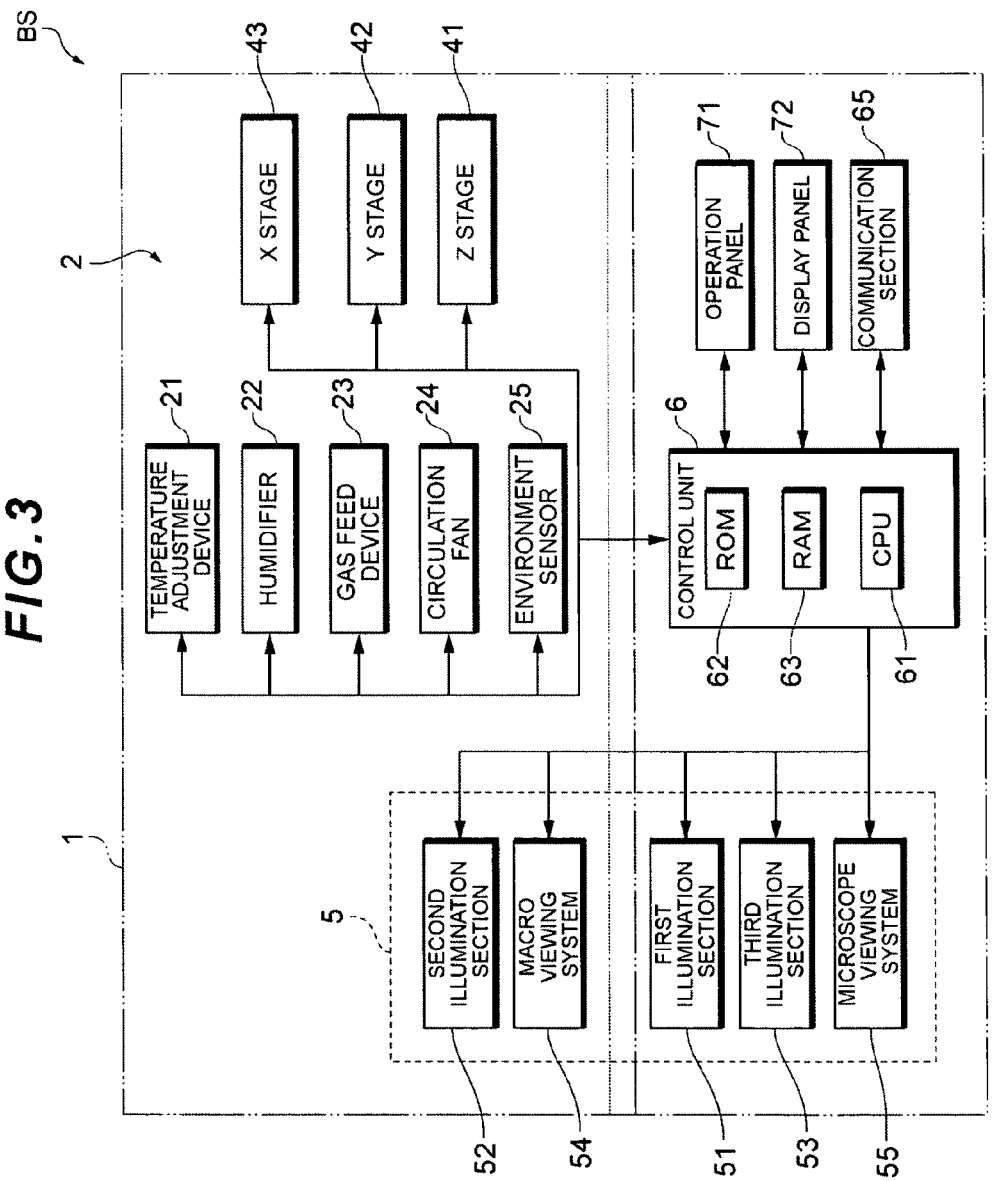

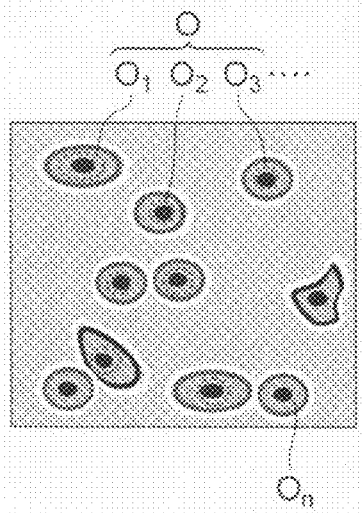
FIG.4A
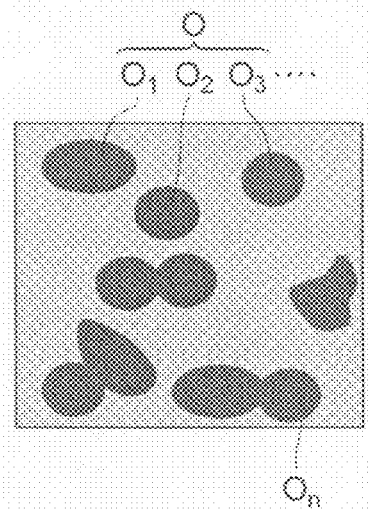
FIG.4B
FIG.5
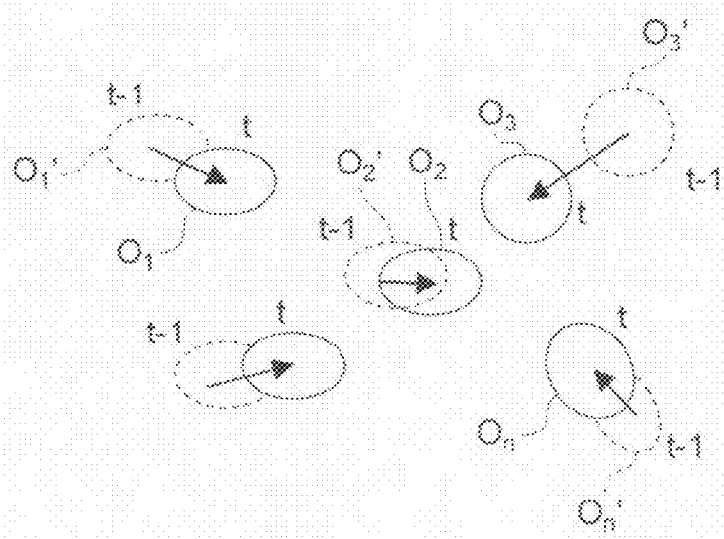

METHOD FOR DISTINGUISHING LIVING CELLS DURING CELL OBSERVATION, IMAGE PROCESSING PROGRAM FOR CELL OBSERVATION, AND IMAGE PROCESSING DEVICE

CROSS-REFERENCE TO RELATED APPLICATIONS

This is a continuation application, under 35 U.S.C. 111(a), of PCT International Application No. PCT/JP2009/053956, filed on Mar. 3, 2009, which is hereby incorporated by reference. This application also claims the benefit of Japanese Patent Application No. 2008-053557, filed in Japan on Mar. 4, 2008, which is hereby incorporated by reference.

TECHNICAL FIELD

Various embodiments described herein relate to image processing means for automatically distinguishing between a living cell and foreign matter from an image obtained during cell observation.

TECHNICAL BACKGROUND

A culture microscope is an example of a device for observing conditions while living cells are being cultured. A culture microscope is provided with a culturing device (incubator) for forming an environment suitable for culturing cells, and a microscope viewing system for performing microscope viewing of the state of cells inside a culture container accommodated in the culturing device. The culture microscope is configured so as to obtain an image of an observed cell at respective predetermined times that have been set in advance, reproduce the obtained images as a continuous projection using, e.g., time-lapse imaging or another technique, and visually ascertain in a simple manner the state of activity of the cells (e.g., see Patent Document 1).

In such a device, foreign matter (non-objects) such as dirt, bubbles, dead cells, and the like may be found together with living cells, which are the observation object in the culture container. Accordingly, a method for distinguishing between observation objects and non-objects when cells are tracked has involved detecting the presence of cell nuclei, cell matter, and the like; and determining whether or not they are living cells.

Patent Document 1: Japanese Laid-open Patent Publication No. 2004-229619

SUMMARY OF THE INVENTION

However, when performing movement analyses of all cells within the observation field of view or at other times when relatively low magnification is used, it is often difficult to detect the texture of the cell nuclei or the like using an observation system in which the internal cell structure is indistinct, and a technique such as that described above cannot be used in such situations.

With the foregoing aspects of the prior art in view, it is an object of the present invention to provide means for making it possible to distinguish between living cells and foreign matter other than living cells during cell observation under broad observation conditions.

In accordance with a first aspect for exemplifying the present invention, there is provided a method for distinguishing living cells during cell observation, comprising, obtaining a first image and a second image of an object (e.g., the object O in the embodiment) positioned in an observation field of view by an imaging device, the first image and the second image being taken at a predetermined time interval; extracting a first representation of the object shown in the first image and a second representation of the object shown in the second image, and aligning the rotational angular orientation of the object in the image plane; computing a correlation value or a difference between the first representation and the second representation in which the rotational angular orientation has been aligned; and determining whether the object is a living cell based on the computed correlation value or difference.

In accordance with a second aspect for exemplifying the present invention, there is provided an image processing program for cell observation, comprising, obtaining a first image and a second image of an object (e.g., the object O in the embodiment) positioned in an observation field of view by an imaging device, the first image and the second image being taken at a predetermined time interval; extracting from the obtained first and second images a first representation of the object shown in the first image and a second representation of the object shown in the second image, and aligning the rotational angular orientation of the object in the image plane; computing a correlation value or a difference between the first representation and the second representation in which the rotational angular orientation has been aligned; determining whether the object is a living cell based on the computed correlation value or difference; and outputting the decision result made in relation to the object.

In accordance with a third aspect for exemplifying the present invention, there is provided an image processing device for cell observation, comprising an imaging device configured to photograph an object (e.g., the object O in the embodiment); an image analysis section obtaining a first image and a second image of an object photographed at a predetermined time interval by the imaging device, and determining whether the object is a living cell from a first representation of the object shown in the first image and a second representation of the object shown in the second image; and an output section outputting a result of a decision made by the image analysis section, wherein the image analysis section is configured so as to extract the first representation and the second representation, align the rotational angular orientation of the object in the image plane, compute a correlation value or a difference between the first representation and the second representation in which the rotational angular orientation has been aligned, and determine whether the object is a living cell based on the computed correlation value or difference.

In accordance with such a method for distinguishing living cells during cell observation, an image processing program for cell observation, and an image processing device for cell observation, an object can be determined to be a living cell using correlations of representations thereof contained in chronological observation images. Therefore, means for enabling living cells to be distinguished from foreign matter other than the living cells can be provided even when observations are made at relatively low magnification, or when using an observation system in which the internal cell structure is indistinct.

BRIEF DESCRIPTION OF THE DRAWINGS

FIG. 3 is a block diagram of the culture observation system;

FIGS. 4A and 4B a schematic view showing by way of example the conditions of contour extraction processing under which a cell contour is extracted;

FIG. 5 is a descriptive view illustrating the association of objects included in the image at time t-1 and objects included in the image at time t;

EXPLANATION OF NUMERALS AND CHARACTERS

Figure 1:
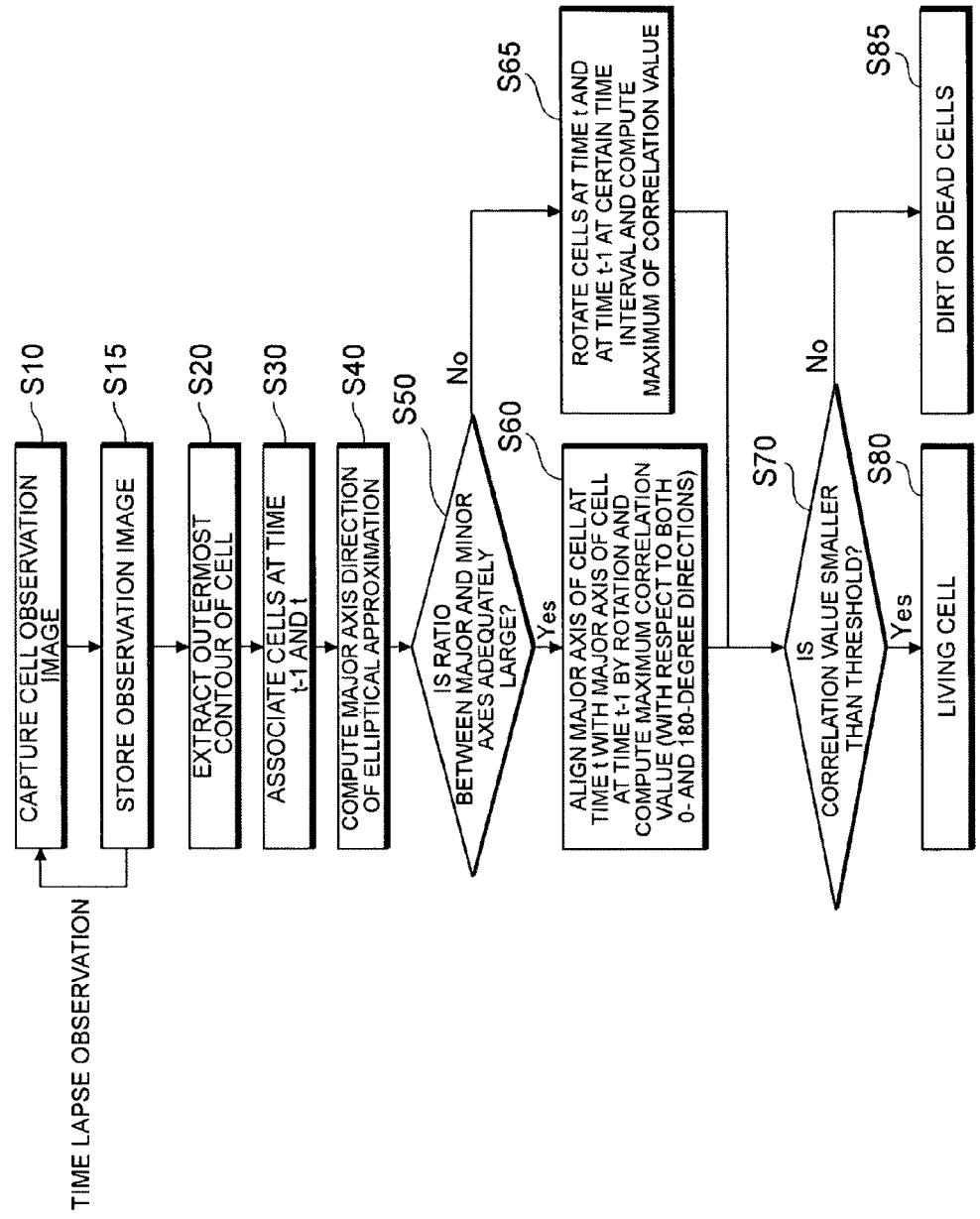
FIG. 1 is a flowchart of the image processing program GP for distinguishing living cells.

BS: Culture observation system
GP: Image processing program
C: Observed cell
54: Macro viewing system
54c: Imaging device
55: Microscope viewing system
55c: Imaging device
100: Image processing device
120: Image analysis section
130: Output section

DESCRIPTION OF THE PREFERRED EMBODIMENTS

Figure 2:
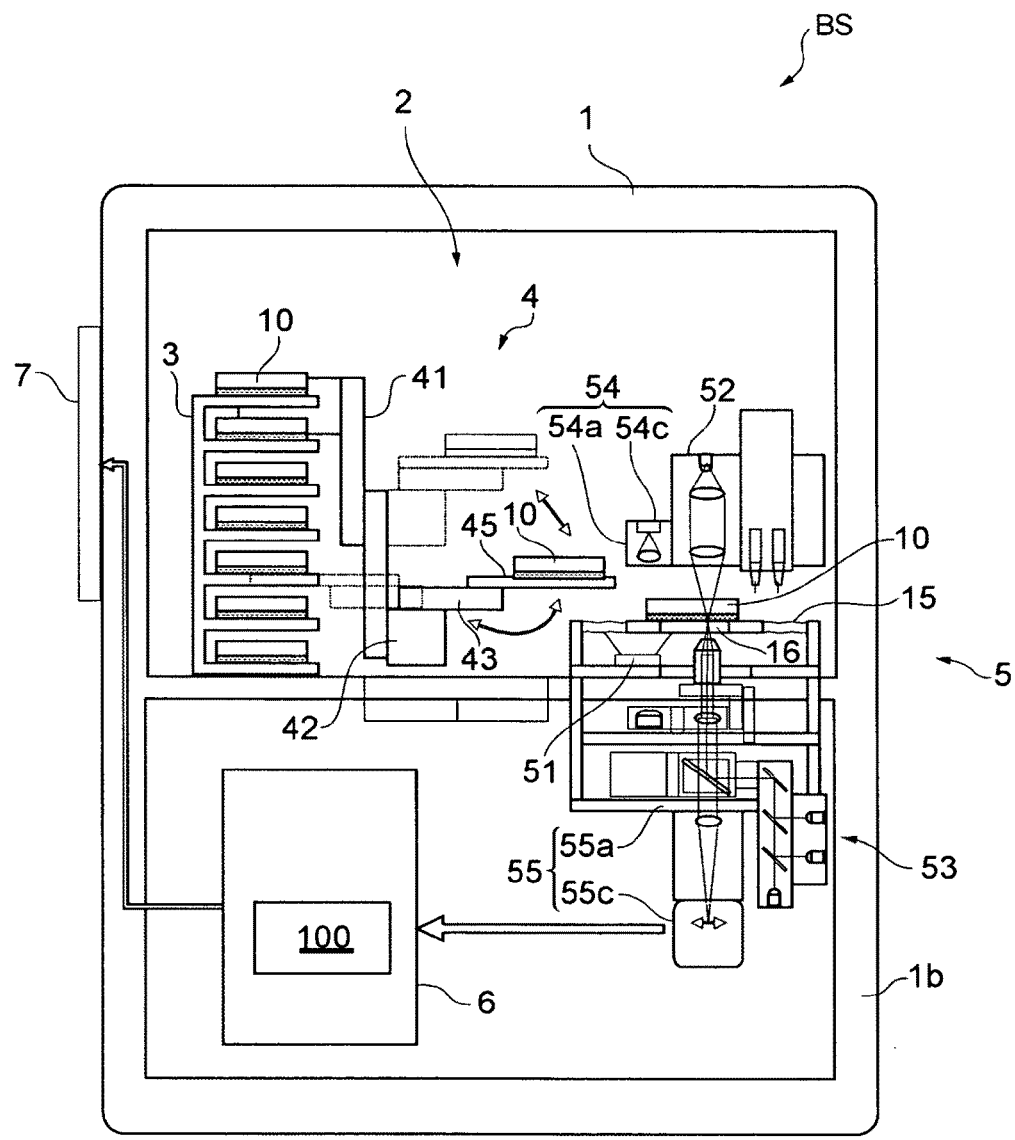
FIG. 2 is a schematic diagram for a culture observation system as an application example of the present invention.

The embodiments of the present invention are described below with reference to the drawings. FIGS. 2 and 3 show a schematic diagram and a block diagram of a culture observation system as an example of a system to which the image processing device for cell observation of the present invention has been applied.

In terms of overall structure, the culture observation system BS is composed of a culture chamber 2 disposed in the upper part of a casing 1, a stocker 3 in a shelf-form configuration for storing and holding a plurality of culture containers 10, an observation unit 5 for observing samples inside the culture containers 10, a transport unit 4 for transporting the culture containers 10 between the stocker 3 and the observation unit 5, a control unit 6 for controlling the operation of the system, and a operation board 7 provided with an image display device.

The culture chamber 2 is a chamber for forming and maintaining a culture environment corresponding to the species, purpose, and other attributes of the cells to be cultured; and the chamber is kept in an airtight state after samples have been loaded in order to prevent changes in the environment and contamination. The culture chamber 2 is equipped with a temperature adjustment device 21 for increasing and reducing the temperature inside the culture chamber; a humidifier 22 for adjusting the humidity; a gas feed device 23 for supplying $CO_2$ gas, $N_2$ gas, or other gases; a circulation fan 24 for keeping the overall environment of the culture chamber 2 uniform; an environment sensor 25 for detecting the temperature, humidity, and the like of the culture chamber 2; and other components. The operation of the devices is controlled by the control unit 6; and the culture environment specified by the temperature, humidity, carbon dioxide concentration, and other attributes of the culture chamber 2 is kept in a state that is consistent with the culture conditions configured using the operation board 7.

The stocker 3 is formed with a plurality of shelves partitioned vertically and perpendicularly with respect to the plane of the diagram of FIG. 2. Each of the shelves is given a unique number. For example, assuming that columns A though C are arranged in the perpendicular direction and shelves 1 through 7 are arranged in the vertical direction, then the shelf in column A, row 5 is designated as "A-5."

The culture containers 10 may be a flask, dish, well plate, or of another type; may be round, angular, or otherwise configured; and may be sized as appropriate. They may be suitably selected and used in accordance with the purpose and species of the cells to be cultured. A configuration in which a dish is used has been given by way of example in the present embodiment. Samples of cells or the like are injected into the culture containers 10 together with a liquid culture medium containing phenol red or another pH indicator. Code numbers are assigned to the culture containers 10 and are stored in accordance with the assigned address in the stocker 3. Container holders for use in transportation, formed in accordance with the type, form, or other parameters of the containers, are mounted on the culture containers 10 and held on the shelves.

A transport unit 4 is composed of a Z stage 41 that is raised by a Z-axis drive mechanism and provided so as to allow movement in the vertical direction inside the culture chamber 2; a Y stage 42 that is moved in the perpendicular direction by a Y-axis drive mechanism and mounted on the Z stage 41 so as to allow movement in the perpendicular direction; an X stage 43 that is moved in the lateral direction by an X-axis drive mechanism and mounted on the Y stage 42 so as to allow movement in the lateral direction; and other components. A support arm 45 for lifting and supporting the culture containers 10 is provided to the distal end side of the X stage 43, which is moved in the lateral direction in relation to the Y stage. The transport unit 4 is configured so that the support arm 45 has a movement range that allows movement between all the shelves of the stocker 3 and a sample stage 15 in the observation unit 5. Each of the X-axis drive mechanism, the Y-axis drive mechanism, and the Z-axis drive mechanism comprises, e.g., a servo motor having a ball screw and an encoder, the operation of each of which drive mechanisms controlled by the control unit 6.

The observation unit 5 is composed of a first illumination section 51, a second illumination section 52, a third illumination section 53, a macro viewing system 54 for observing samples macroscopically, a microscope viewing system 55 for observing samples microscopically, an image processing device 100, and other components. The sample stage 15 is composed of a translucent material, and a transparent window section 16 is provided to the observation region of the microscope viewing system 55.

The first illumination section 51 is composed of a plane-emission light source provided to a lower frame 1b, and provides backlighting to all the culture containers 10 from the lower side of the sample stage 15. The second illumination section 52 has an illumination system composed of LEDs or another light source, and a phase ring, condenser lens, and the like; is provided to the culture chamber 2; and is used for illuminating the samples in the culture containers from above the sample stage 15 along the optical axis of the microscope viewing system 5. The third illumination section 53 has an illumination optical system composed of a plurality of LEDs, a mercury lamp, or other light sources for emitting light at a wavelength suited to epi-illumination observation or fluorescent observation; and a beam splitter, a fluorescent filter, or the like for superimposing light emitted from the light sources onto the optical axis of the microscope viewing system 55. The third illumination section 53 is disposed inside the lower frame 1b positioned on the lower side of the culture chamber 2; and illuminates the samples in the culture containers along the optical axis of the micro observation unit 5 from below the sample stage 15.

The macro viewing system 54 has an observation optical system 54a and a CCD camera or another imaging device 54c for photographing representations of the samples imaged by the observation optical system, and is disposed inside the culture chamber 2 positioned above the first illumination section 51. The macro viewing system 54 photographs an overall observation image (macro representation) from above the culture containers 10 backlit by the first illumination section 51.

The microscope viewing system 55 is disposed inside the lower frame 1b, and has an observation optical system 55a composed of an objective, a middle zooming lens, a fluorescent filter, and the like; and a cooled CCD camera or another imaging device 55c for photographing representations of the samples imaged by the observation optical system 55a. The objective and middle zooming lens are provided in a plural number, and are configured so that a plurality of magnifications can be set using a revolver, a slider, or another displacement mechanism (not shown) and the magnification can be varied within a range of, e.g., 2× to 80× in accordance with an initially selected lens setting. The microscope viewing system 55 obtains a microscopically observed representation (i.e., a micro representation), obtained by microscopically observing transmitted light illuminated by the second illuminating part 52 and transmitted through the cell, reflected light illuminated by the third illuminating part 53 and reflected by the cell, or fluorescent light emitted by the cell when illumination has been provided by the third illuminating part 53.

The image-processing device 100 performs an analog-to-digital conversion on a signal inputted from the imaging device 54c of the macro viewing system and the imaging device 55c of the microscope viewing system, performs a variety of types of image processing, and generates image data for the overall observed image or the microscopically observed image. The image-processing device 100 also performs image analysis on the image data for the observed images, generates a time-lapse image, calculates cell travel, analyzes the cell movement state, or performs other tasks. Specifically, the image-processing device 100 is configured by executing an image-processing program stored in a ROM of the control unit 6 described below. The image-processing device 100 will be described in detail further below.

The control unit 6 comprises a CPU 61; a ROM 62 having configured and stored therein a control program for controlling the operation of the culture observation system BS, or data for controlling a variety of components; a RAM 63 for temporarily storing image data and other data; and other devices. In the control unit 6, the devices are connected by a data bus. Connected to an input/output port of the control unit 6 are the temperature regulating device 21, the humidifier 22, the gas feed device 23, the circulation fan 24, and the environment sensor 25 provided to the culture chamber 2; each of the X-, Y-, and Z-axis driving mechanisms for driving the X, Y, Z stages 43, 42, 41 provided to the transport unit 4; the first, second, and third illumination sections 51, 52, 53, the macro viewing system 54, and the microscope viewing system 55 provided to the observation unit 5; a operation panel 71 and a display panel 72 provided to the operation board 7; and other devices. A detection signal is inputted from each of the devices listed above into the CPU 61, and each of the devices is controlled in accordance with a control program stored in advance in the ROM 62.

The operation panel 7, to which is provided a keyboard, a sheet switch, and an input/output device such as a read/write device for reading information from, and writing information to, a magnetic recording medium, an optical disc, or another medium; and the display panel 72, for displaying a variety of operation screens, image data, and other information, are provided to the operation board 7. The user configures an observation program (operating conditions), selects conditions, and enters an operation command or other information using the operation panel 71 while referring to the display panel 72, and thereby operates, via the CPU 61, the devices provided to the culture observation system BS. In other words, in accordance with what is input from the operation panel 71, the CPU 61 adjusts the environment in the culture chamber 2; transports the culture container 10 within the culture chamber 2; observes the sample using the observation unit 5; analyzes obtained image data; displays information on the display panel 72; and performs other operations. The display panel 72 displays numerical values representing environmental conditions in the culture chamber 2, analyzed image data, alerts in the event of a fault, and the like in addition to other input screens for operation commands, condition selections, and the like. The CPU 61 is able to transmit and receive data to and from an externally connected computer or another device via a communication section 65 compliant with wired or wireless telecommunication standards.

The temperature, humidity, or other environmental conditions in the culture chamber 2; an observation schedule for each of the culture containers 10; the type, position, magnification, and other observation conditions associated with the observation unit 5; and other operation conditions for the observation program configured using the operation panel 71 are stored in the RAM 63. The code number for each of the culture containers 10 accommodated in the culture chamber 2, the storage address of the culture container 10 in the stocker 3 corresponding to each code number, and other management data for managing the culture container 10; and a variety of data used for the image analysis are also stored in the RAM 63. The RAM 63 is provided with an image data storage region (image storage section 110, described hereinafter) for storing data relating to images obtained using the observation unit 5. Indexing data, containing the code number of the culture container 10, the date and time when the image was obtained, and similar information, is stored in correlation with the image data.

In the culture observation system BS configured as above, the CPU 61 controls the operation of each of the devices based on the control program stored in the ROM 62 and automatically obtains an image of the sample in the culture container 10, according to the conditions set for the observation program as entered using the operation board 7. In other words, when operation of the operation panel 71 (or remote operation via the communication section 65) starts the observation program, the CPU 61 reads the value of each of the environmental conditions stored in the RAM 63; detects the environmental state in the culture chamber 2 inputted from the environment sensor 25; operates the temperature adjustment device 21, the humidifier 22, the gas feed device 23, the circulation fan 24, and similar devices according to the difference between the condition value and the actual value; and performs feedback control on the temperature, humidity, carbon dioxide concentration, and other culture environment conditions in the culture chamber 2.

The CPU 61 reads the observation conditions stored in the RAM 63, operates each of the X-, Y-, and Z-axis driving mechanisms for driving the X, Y, Z stages 43, 42, 41 provided to the transport unit 4 and transports the culture container 10 corresponding to the observed object from the stocker 3 to the sample stage 15 in the observation unit 5 according to an observation schedule, and starts observation of the observed object by the observation unit 5. For example, in an instance where the observation program has been set for macroscopic viewing, the culture container 10 conveyed by the conveying unit 4 from the stocker 3 is positioned on an optical axis of the macro viewing system 54 and placed on the sample stage 15, the light source of the first illuminating part 51 is illuminated, and the imaging device 54c is used to obtain an overall observed representation from above the backlit culture container 10. A signal sent from the imaging device 54c into the control unit 6 is processed by the image-processing device 100, an overall observed representation is generated, and the image data is stored in the RAM 63 together with the indexing data, such as the date and time when the image was obtained, and other information.

In an instance where the observation program has been set for microscopic viewing of a sample at a specific location in the culture container 10, the specific location in the culture container 10 transported by the transport unit 4 is positioned on an optical axis of the microscope viewing system 55 and placed on the sample stage 15, the light source of the second illuminating part 52 or the third illuminating part 53 is illuminated, and the imaging device 55c is used to obtain a transmission-illuminated, epi-illuminated, or fluorescence-assisted microscopically observed representation. A signal obtained when an image is obtained by the imaging device 55c and sent to the control unit 6 is processed by the image-processing device 100, a microscopically observed representation is generated, and the image data is stored in the RAM 63 together with the indexing data, such as the date and time when the image was obtained, and other information.

The CPU 61 performs the observation described above on a plurality of samples in culture containers accommodated in the stocker 3, wherein the overall observed representation or the microscopically observed representation is successively obtained according to an observation schedule having a time interval of about 30 minutes to 2 hours based on the observation program. According to the present embodiment, the time interval between obtained images may be fixed or variable. The image data for the overall observed representation or the microscopically observed representation that has been obtained is stored together with the code number of the culture container 10 in the image data storage region (image storage section 110) of the RAM 63. The image data stored in the RAM 63 is read from the RAM 63 according to an image display command inputted from the operation panel 71, and an overall observed representation or a microscopically observed representation for a specified time (i.e., a single image), or a time-lapse image of overall observed representations or microscopically observed representations from a specified time region, are displayed on the display panel 72 of the operation board 7.

In the culture observation system BS thus configured, the image processing device 100 is not only provided with functions for analyzing cell movement and tracking cells, but also with a function for distinguishing between living cells as the observation object and foreign matter (non-objects) such as dirt, bubbles, dead cells, and other articles that are not the living cells, in order for the other functions to be efficiently performed.

The method for distinguishing living cells carried out by the image processing device 100 is designed so that two images of an object positioned inside the observation field of view of the observation unit 5 are obtained and photographed at predetermined times using an imaging device, a representation of the object shown in the images is extracted, the rotational angular orientation (cell orientation angle) of the object in the image plane is aligned, the difference or the correlation value of the two images is computed, and the correlation values or the difference thus computed is used to determine whether the object is a living cell.

(Preprocessing)

The outermost contour of objects O (the region of the living cell or of articles including dirt or other foreign matter; hereinafter referred to as "objects") contained in an image is extracted before the process for distinguishing living cells is carried out. FIG. 4 is a schematic view exemplifying the state of the process for extracting the outermost contour. The image (a) at time t photographed by the imaging device 55c (54c) (referred to as "first image" for convenience) and the image at time t-1 photographed at a predetermined time earlier than the first image (similarly, referred to as "second image") are obtained, and the outermost contours of the objects O are extracted from the images as shown in (b). Examples of the method for this extraction include dynamic contour extraction methods such as luminance-based binarization, binarization following application of a dispersion filter, and snakes or level set methods. The predetermined time is set in accordance with the movement state of the living cells as the observation object. For example, the predetermined time is about 10 minutes to 1 hour in the case the movement of the living cells is relatively high, and is 30 minutes to 2 hours in the case that the movement of the living cells is relatively low.

The objects O thus segmented are labeled in a correspondence relationship of $O_1, O_2, O_3 \ldots O_n$, contained in the first image and $O_1', O_2', O_3', \ldots O_n'$ contained in the second image. For example, the objects that have been labeled are placed in a correspondence relationship by letting the labels nearest to each other refer to the same object, and are associated in the manner of $O_1$ and $O_1'$, $O_2$ and $O_2'$, $O_3$ and $O_3'$, ..., $O_n$ and $O_n'$ as shown in FIG. 5 wherein the objects in the first image are shown as solid lines and the objects in the second image are shown as dotted lines.

(Distinguishing Living Cells)

Next, for the associated objects, the rotational angular orientation (cell orientation angle) of the representation of the objects of the first image (referred to as first representation) and the representation of the objects of the second image (referred to as second representation) are aligned in the image plane. As a specific method, the second moment of area (moment of inertia) about the axis that passes through the centroid (center of gravity) is computed for each of the associated objects (e.g., $O_1$ and $O_1'$), and the rotational angular orientation of the first representation and the second representation is aligned in an angular position in which the correlation value between the second moment of area of the first representation $I_1$ and the second moment of area of the second representation $I_2$ is at a maximum. In an alternative configuration, the objects O are approximated to an elliptical shape, and the major axis directions of the approximated elliptical models are aligned. In the case that the contour shapes of the objects approximate a circle, the correlation between the two representations is computed while one of the two representations is rotated at fixed angles about the axis that passes through the centroid to achieve alignment at an angle at which the correlation values are at a maximum.

Also possible is a configuration in which the rotational angular orientations are aligned at an angle at which the difference between the second moment of area of the first representation $I_1$ and the second moment of area of the second representation $I_2$ is at a minimum. Alternatively, the difference between the two representations is computed while one of the two representations is rotated at fixed angles about the axis that passes through the centroid to achieve alignment at an angle at which the difference is at a minimum.

Figure 6:
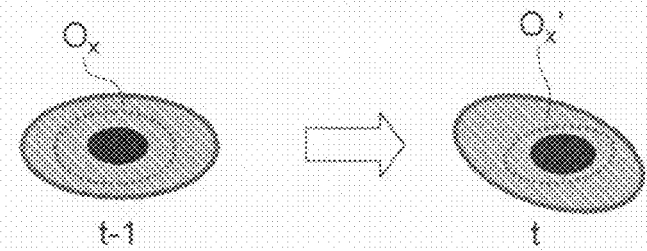
FIG. 6 is a schematic view illustrating the change in state of the living cells from time t-1 to time t.
Figure 7:
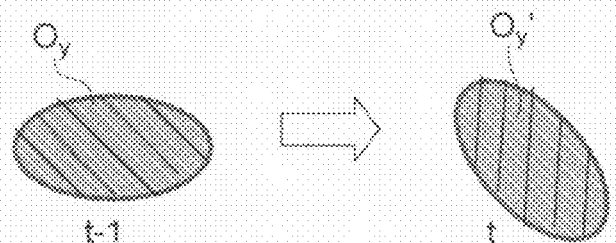
FIG. 7 is a schematic view illustrating the change in state of objects other than living cells from time t-1 to time t.

Therefore, when the object $O_x$ for which a correlation is computed is a living cell, not only does the outer shape change with the passage of time, but the internal structure also changes from $O_x$ to $O_x'$, as shown in FIG. 6. Accordingly, the correlation values of the first representation and the second representation do not become very large, typically being 0.7 or less. In contrast, when the object $O_y$ for which a correlation is computed is foreign matter such as dirt, bubbles, dead cells, or the like, a change in structure with respect to time substantially does not occur from $O_y$ to $O_y'$, as shown in FIG. 7. Accordingly, the correlation value of the first representation and the second representation in which the rotational angular orientations have been aligned is high and is approximately 1.

Therefore, it is possible to determine whether an object is a living cell or foreign matter such as dirt, bubbles, dead cells, or the like by aligning the rotational angular orientations of associated objects, computing the correlation value, and determining whether the computed correlation value is less than a predetermined threshold. A suitable value may be selected as the "predetermined threshold" in accordance with the cell species, the state of activity, and the time interval for carrying out observations, or another parameter; and may be selected and set in a range of, e.g., about 0.5 to 0.8.

Figure 8:
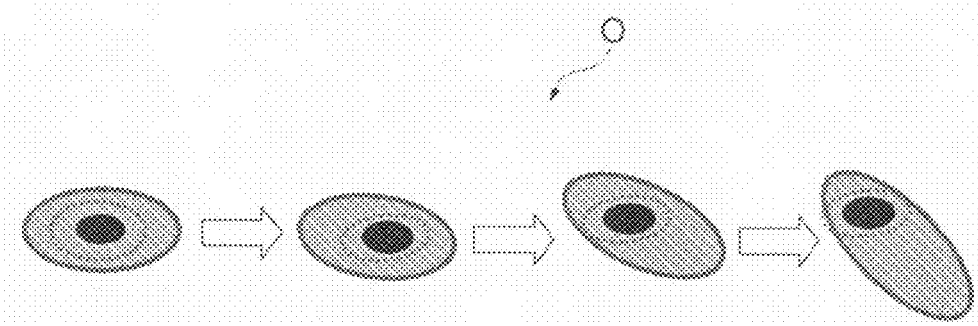
FIG. 8 is a schematic view illustrating the change in state of the living cells as time elapses.
Figure 9:
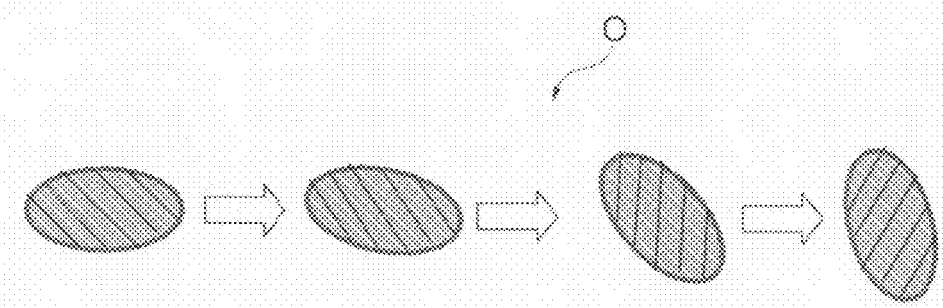
FIG. 9 is a schematic view illustrating the change in state of objects other than living cells as time elapses.

As means for increasing the distinguishing accuracy, a method is proposed in which the period treated as a time series (time interval) is lengthened, and a mutual correlation is obtained by tracking over a sufficient amount of time. According to such a method, the correlation value decreases over time when the object O is a living cell, as shown in FIG. 8, while the correlation value remains approximately 1 even over the course of time when the object O is foreign matter, as shown in FIG. 9. The difference in correlation values between a living cell and foreign matter is readily apparent. Therefore, the living cells and foreign matter can be readily separated by the threshold and distinguishing accuracy can be improved.

Figure 10:
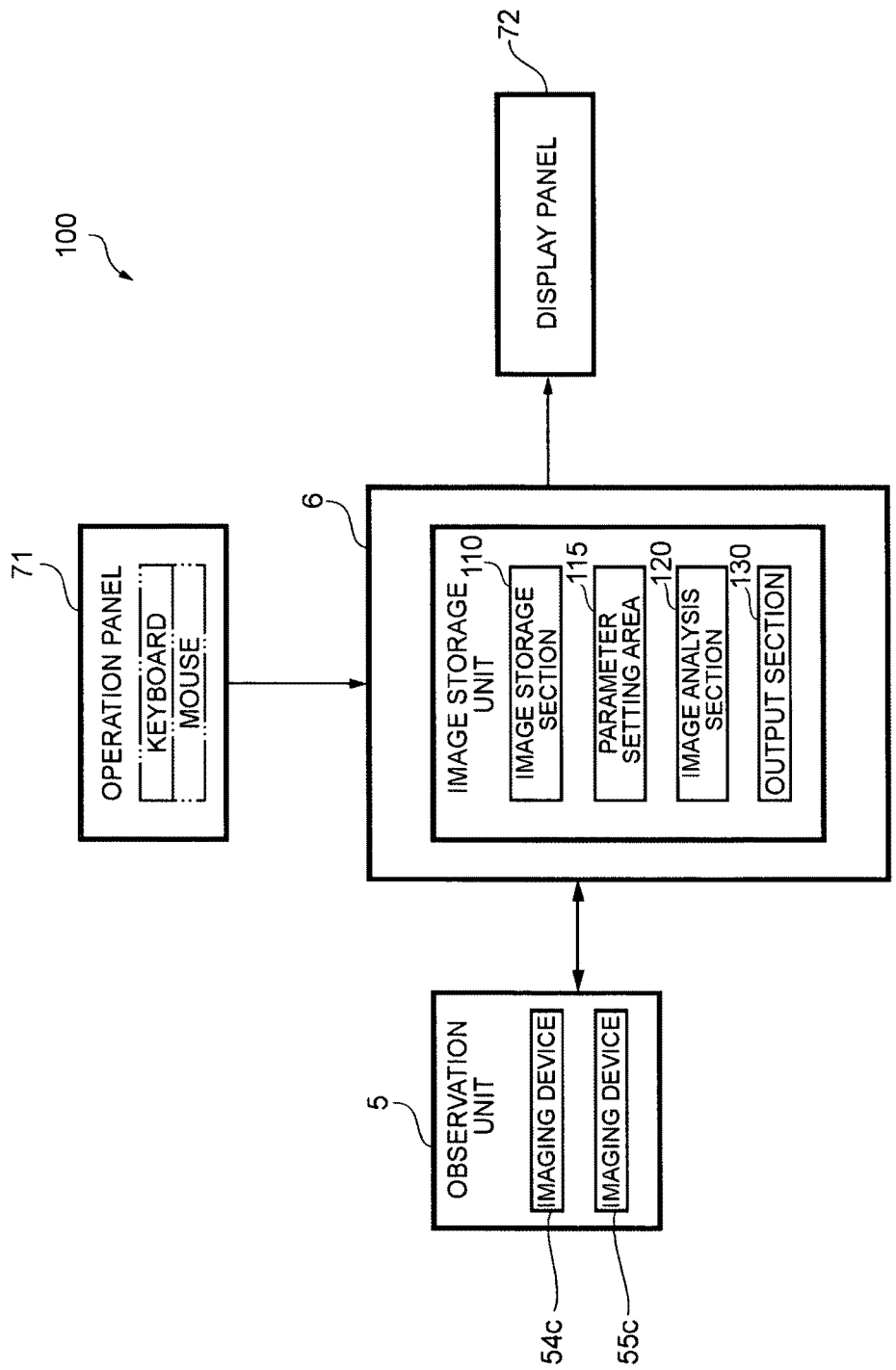
FIG. 10 is a block view showing the general configuration of the image processing device.

Next, a specific application of image analysis carried out by the image processing device 100 of the culture observation system BS will be described with reference to FIGS. 1 and 10. FIG. 10 is a block view showing the general configuration of the image processing device 100 for processing images for distinguishing living cells; and FIG. 1 is a flowchart of the image processing program GP for distinguishing living cells.

The image processing device 100 is provided with an image storage section 110 for capturing and storing a first image and a second image photographed at a predetermined time interval using the imaging device 55c (54c), an image analysis section 120 for determining whether or not an object O is a living cell, from a first representation of the object shown in the first image and a second representation of the object shown in the second image, and an output section 130 for outputting to the exterior the result of the decision made by the image analysis section 120. The result of the decision made by the image analysis section 120 as to whether an object is a living cell is configured so as be outputted and displayed on, e.g., the display panel 72. The image processing device 100 is configured so that the image processing program GP set and stored in advance in the ROM 62 is read by the CPU 61, and processing based on the image processing program GP is carried out in a sequential fashion by the CPU 61.

The image analysis processing carried out by the image analysis section 120 can read a plurality of image data photographed at a predetermined time interval and stored in advance in the image storage section 110 (image storage area of the RAM 63), but can also obtain from the imaging device observation data obtained from ongoing observation. Described in the present embodiment is the case in which a decision is made as to whether an object contained in an image photographed by the imaging device is a living cell, the decision being made in the process for microscopically observing cells inside a specified culture container 10 at predetermined times, in accordance with an observation program set in advance.

A described above, in the culture observation system BS, cells inside a specified culture container are observed at predetermined intervals in accordance with observation conditions set in an observation program. Specifically, the CPU 61 actuates the drive mechanisms of the shafts of the transport unit 4, transports the culture container 10 to be observed from the stocker 3 to the observation unit 5, and causes the imaging device 55c to photograph the observation representation produced by the microscope viewing system 55.

In step S10, the image processing device 100 obtains the observation image photographed by the imaging device 55c. In step S15, the obtained observation image is stored in the image storage section 110 together with the code number of the culture container, the observation position, observation time, and other index data; and the process the proceeds to step S20. The image processing device 100 repeatedly executes the capturing of the observation image (step S10) and the saving (step S15) thereof in the image storage section 110 at predetermined times in accordance with the observation program.

In step S20, the image analysis section 120 carries out a process in for extracting the outermost contour of an object from the observation image at time t obtained using the imaging device 55c (first image) and the observation image photographed by the imaging device at time t-1 a predetermined time earlier and stored in the image storage section 110 (second image). The outermost contour of the object O contained in the observation image is extracted, as shown in FIG. 4(b), and the process proceeds to step S30.

In step S30, the objects O in the first and second images from which the outermost contours were extracted are labeled, and a correspondence relationship between the objects in the first image (solid lines: $O_1, O_2, O_3 \ldots O_n$) and the objects in the second image (dotted lines: $O_1', O_2', O_3', \ldots O_n'$) is formed so that the labels nearest to each other are regarded to be the same object and associated ($O_1$ and $O_1'$, $O_2$ and $O_2'$, $O_3$ and $O_3'$, . . . , $O_n$ and $O_n'$), as shown in, e.g., FIG. 5.

Next, for the associated objects; e.g., $O_n$ and $O_n'$, the rotational angular orientations of the first representation of the object $O_n$ of the first image and the second representation of the object $O_n'$ of the second image in the image plane are aligned, and the correlation value of the first representation and the second representation is computed.

In the configuration example illustrated in FIG. 1, in step S40, an elliptical approximation is made for the first representation of the object $O_n$ and the second representation of the object $O_n'$, the major axis directions (or the minor axis directions) of the approximation ellipses are computed, the ratio between the major and minor axes of the approximation ellipses is computed, and a decision is made as to whether the ratio between the major and minor axes of the ellipses computed in step S50 is sufficiently high. If the ratio between the major and minor axes (major axis length/minor axis length) of the ellipses computed in step S40 is sufficiently greater than 1 (e.g., when the ratio is 2 or higher), the rotational angular orientations (directional angles) of the objects can be made to coincide in a highly precise manner by aligning the long-axis directions of the approximation ellipses, even if outer shape deformation of the living cells is taken into account.

However, if the ratio between the major and minor axes is approximately 1, the object will have a substantially round contour, and methods for aligning the major axis directions of ellipses will not have the adequate precision for matching the rotational angular orientations of the living cells. Accordingly, a decision as to whether the ratio between the major and minor axes of approximate ellipses is sufficiently high is made in step S50. If the ratio between the major and minor axes is sufficiently high, the process proceeds to step S60, whereas otherwise the process proceeds to step S65. The reference value used to judge the ratio between the major and minor axes is stored in a parameter setting area 115 of the RAM 63 and can be modified and set via the operation panel 71 in accordance with the object to be observed. The reference value for judging the approximation of an elliptical shape need not merely be a simple ratio of the major axis and the minor axis; it may be the difference between the major axis and the minor axis, the length of the minor axis or the major axis/(minor axis length+major axis length), or another reference that allows differentiation to be made between an ellipse and a circle.

In step S60, the correlation value is computed in a state in which the major axis directions of the ellipse that approximates the first representation of the object $O_n$ (referred to as "first ellipse") and the ellipse that approximates the second representation of the object $O_n'$ (referred to as "second ellipse") have been aligned, whereby the rotational angular orientation of the first representation and the rotational angular orientation of the second representation have been aligned. Since there are cases in which the major axis direction of the ellipse is oriented in the left-right direction on the centroid and the top and bottom of the cell are facing in opposite directions, correlation values are computed for both the 0-degree and 180-degree directions, and the larger of these correlation values is used as the correlation value of the first representation and the second representation, whereupon the process proceeds to step S70.

In step S65, the first representation or the second representation is rotated about the centroid at fixed-angle intervals, during which the correlation value is computed in each of the angular positions. For example, the first representation of the object $O_n$ at time t is rotated 360 degrees at fixed angles of about 5 to 10 degrees about the centroid, and calculations are made of the correlation value with the second representation of the object $O_n'$ at time t-1 in each of the angular positions. The correlation value of the angular position having the maximum correlation value is used as the correlation value of the first representation and the second representation, and the process proceeds to step S70.

In step S70, it is determined whether the correlation value of the first representation and the second representation used in step S60 or step S65 is less than a predetermined threshold. As described with contrasting reference to FIGS. 6 and 7, in the case that the objects $O_n$ and $O_n'$ are living cells, the outer shape and the internal structure change over time; therefore, while the first representation and the second representation have a fixed correlation in being the same cell, the correlation value is not very large; i.e., is typically 0.7 or less. On the other hand, in the case that the objects $O_n$ and $O_n'$ are dirt, bubbles, dead cells, or the like, the outer shape and internal structure do not substantially change over time, so that the correlation value of the first representation and the second representation is near 1.

The "predetermined threshold" above is a judgment reference value set in view of the difference between correlation values of living cells and foreign matter other than living cells, as indicated above. A threshold of about 0.6 to 0.7 is selected in common time lapse observation of living cells and is set and stored in the parameter setting area 115 of the RAM 63. The optimum threshold varies slightly in accordance with the species of living cells under observation, the state of activity, the time interval at which observations are carried out, and other observation conditions. Accordingly, the configuration in the image processing device 100 allows the threshold to be modified and set in accordance with the observation conditions, and may be modified and set in a range of, e.g., about 0.5 to 0.8 by using the operation panel 71 to retrieve and modify the judgment reference threshold.

The living cell judgment reference is not limited to being the correlation value of the first representation and the second representation, but may also be the difference between the first representation and the second representation, or may be another reference. If the difference is used, the threshold may be empirically set in accordance with the observation conditions.

Thus, in step S70, a decision is made as to whether the correlation value of the first representation of the object $O_n$ and the second representation of the object $O_n'$ is less than the predetermined threshold. In the case that the correlation value is determined to be less than the predetermined threshold, a decision result indicating that the objects $O_n$, $O_n'$ are living cells is outputted from the output section 130 in step S80, and in the case that the correlation value is determined to be equal to or greater than the predetermined threshold, a decision result indicating that the objects $O_n$, $O_n'$ are not living cells is outputted from the output section 130 in step S85.

The image processing device 100 executes the processing described above for the objects $O_1$, $O_2$, $O_3$, $O_n$ contained in the first image and the second image, and the output section 130 outputs a decision result for each of the objects. The decision result for each of the objects outputted from the output section 130 is displayed on the display panel 72 of the operation board 7, and the display shows whether or not the objects $O_1$, $O_2$, $O_3$, $O_n$ are living cells in the first image photographed at time t, or both the first image at time t and the second image at time t-1.

Figure 11:
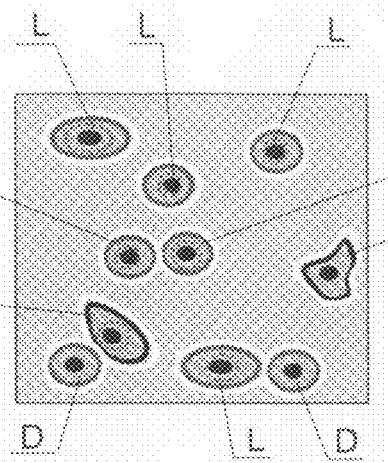
FIG. 11 is a schematic view (1) illustrating the display for differentiating between living cells and foreign matter.
Figure 12:
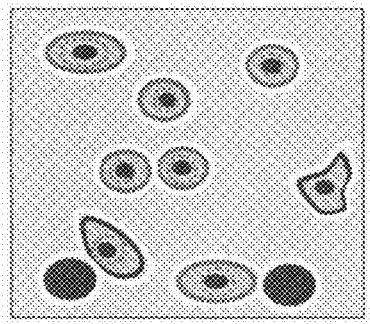
FIG. 12 is a schematic view (2) illustrating the display for differentiating between living cells and foreign matter.

As a specific display mode, for example, the reference symbol L indicating that an object is a living cell and the reference symbol D indicating that an object is foreign matter is additionally displayed as shown in FIG. 11. Other interface examples include using different colors to display and distinguish between living cells and foreign matter, displaying the foreign matter filled in as shown in FIG. 12, removing the foreign matter from the displayed image, or using another mode to differentiate and display living cells and foreign matter other than living cells. It is also possible to use a configuration in which the aforedescribed differentiation data outputted from the output section 130 is transmitted to an externally connected computer or the like via the communication section 65 and the same image is displayed, or a configuration in which basic data for performing cell movement analyses, cell tracking, or other tasks is used.

An observer can thereby refer to the image displayed on the display panel 72 or on the display device of an externally connected computer or the like to promptly discern whether an object contained in the images under observation (or images that have already been obtained) is a living cell or not. By using data in which living cells and foreign matter have been differentiated as described above, image processing can be used to perform efficient movement analyses or tracking of living cells independently of foreign matter.

As described above, in accordance with the image processing program GP, the method for distinguishing living cells constituted by executing the image processing program, and the image processing device 100 of the present invention, correlations of object representations contained in observation images presented in a time series can be used to determine whether an object is a living cell. Therefore, it is possible to identify living cells from dirt, dead cells, and other foreign matter even when observations are made at relatively low magnification, or when the internal cell structure is not readily discernable with the observation system employed. It is therefore possible to provide means for enabling living cells to be distinguished from foreign matter other than living cells when observing cells under broad observation conditions.

The many features and advantages of the embodiments are apparent from the detailed specification and, thus, it is intended by the appended claims to cover all such features and advantages of the embodiments that fall within the true spirit and scope thereof. Further, since numerous modifications and changes will readily occur to those skilled in the art, it is not desired to limit the inventive embodiments to the exact construction and operation illustrated and described, and accordingly all suitable modifications and equivalents may be resorted to, falling within the scope thereof.

What is claimed is:

1. A method for distinguishing living cells during cell observation, comprising:
    obtaining a first image and a second image of an object positioned in an observation field of view by an imaging device, the first image and the second image being taken at a predetermined time interval;
    extracting a first representation of the object shown in the first image and a second representation of the object shown in the second image, and aligning the rotational angular orientation of the object in the image plane;
    computing a correlation value or a difference between the first representation and the second representation in which the rotational angular orientation has been aligned; and
    determining whether the object is a living cell based on the computed correlation value or difference.

2. The method for distinguishing living cells during cell observation according to claim 1, wherein the rotational angular orientation of the object is aligned with an angle at which the correlation value between a second moment of area of the first representation and a second moment of area of the second representation is at a maximum.

3. The method for distinguishing living cells during cell observation according to claim 1, wherein the rotational angular orientation of the object is aligned with an angle at which a difference between a second moment of area of the first representation and a second moment of area of the second representation is at a minimum.

4. The method for distinguishing living cells during cell observation according to claim 1, wherein the rotational angular orientation of the object is aligned with an angle at which the correlation value between the first representation and the second representation is at a maximum when the correlation between the first representation and the second representation is calculated while the first representation or the second representation is rotated about an axis that passes through a centroid.

5. The method for distinguishing living cells during cell observation according to claim 1, wherein the rotational angular orientation of the object is aligned with an angle at which the difference between the first representation and the second representation is at a minimum when the difference between the first representation and the second representation is calculated while the first representation or the second representation is rotated about an axis that passes through a centroid.

6. A non-transitory computer-readable medium encoded with an image processing program for cell observation, the program when executed by a computer causes the computer to perform a method comprising:
    obtaining a first image and a second image of an object positioned in an observation field of view by an imaging device, the first image and the second image being taken at a predetermined time interval;
    extracting, from the obtained first and second images, a first representation of the object shown in the first image and a second representation of the object shown in the second image, and aligning the rotational angular orientation of the object in the image plane;
    computing a correlation value or a difference between the first representation and the second representation in which the rotational angular orientation has been aligned;
    determining whether the object is a living cell based on the computed correlation value or difference; and
    outputting the decision result made in relation to the object.

7. The non-transitory computer-readable medium according to claim 6, wherein the rotational angular orientation of the object is aligned with an angle at which the correlation value between a second moment of area of the first representation and a second moment of area of the second representation is at a maximum.

8. The non-transitory computer-readable medium according to claim 6, wherein the rotational angular orientation of the object is aligned with an angle at which a difference between a second moment of area of the first representation and a second moment of area of the second representation is at a minimum.

9. The non-transitory computer-readable medium according to claim 6, wherein the rotational angular orientation of the object is aligned with an angle at which the correlation value between the first representation and the second representation is at a maximum when the correlation between the first representation and the second representation is calculated while the first representation or the second representation is rotated about an axis that passes through a centroid.

10. The non-transitory computer-readable medium according to claim 6, wherein the rotational angular orientation of the object is aligned with an angle at which the difference between the first representation and the second representation is at a minimum when the difference between the first representation and the second representation is calculated while the first representation or the second representation is rotated about an axis that passes through a centroid.

11. An image processing device for cell observation, comprising:
    an imaging device configured to photograph an object;
    an image analysis section obtaining a first image and a second image of an object photographed at a predetermined time interval by the imaging device, and determining whether the object is a living cell from a first representation of the object shown in the first image and a second representation of the object shown in the second image; and an output section outputting a result of a decision made by the image analysis section, wherein the image analysis section is configured to extract the first representation and the second representation, align the rotational angular orientation of the object in the image plane, compute a correlation value or a difference between the first representation and the second representation in which the rotational angular orientation has been aligned, and determine whether the object is a living cell based on the computed correlation value or difference.

12. The image processing device for cell observation according to claim 11, wherein the rotational angular orientation of the object is aligned with an angle at which the correlation value between the second moment of area of the first representation and the second moment of area of the second representation is at a maximum.

13. The image processing device for cell observation according to claim 11, wherein the rotational angular orientation of the object is aligned with an angle at which a difference between a second moment of area of the first representation and a second moment of area of the second representation is at a minimum.

14. The image processing device for cell observation according to claim 11, wherein the rotational angular orientation of the object is aligned with an angle at which the correlation value between the first representation and the second representation is at a maximum when the correlation between the first representation and the second representation is calculated while the first representation or the second representation is rotated about an axis that passes through a centroid.

15. The image processing device for cell observation according to claim 11, wherein the rotational angular orientation of the object is aligned with an angle at which the difference between the first representation and the second representation is at a minimum when the difference between the first representation and the second representation is calculated while the first representation or the second representation is rotated about an axis that passes through a centroid.

* * * * *